United States Patent [19]

Solanki

[11] Patent Number: 5,262,175
[45] Date of Patent: Nov. 16, 1993

[54] STABILIZATION OF RADIOPHARMACEUTICAL COMPOSITIONS

[76] Inventor: Kishor K. Solanki, 76 Chapter Road, London, NW2 5LN, England

[21] Appl. No.: 899,238

[22] Filed: Jun. 16, 1992

Related U.S. Application Data

[63] Continuation of Ser. No. 521,138, May 8, 1990, abandoned.

[30] Foreign Application Priority Data

May 10, 1989 [GB] United Kingdom ............... 8910779

[51] Int. Cl.$^5$ .................. A61K 43/00; A61K 49/02
[52] U.S. Cl. .................................. 424/1.1; 514/970
[58] Field of Search ........................... 424/1.1; 534/14

[56] References Cited

U.S. PATENT DOCUMENTS

| | | | |
|---|---|---|---|
| 4,342,740 | 8/1982 | Narra et al. | 424/1.1 |
| 4,431,627 | 2/1984 | Eckelman et al. | 424/1.1 |
| 4,444,743 | 4/1984 | Yokoyama et al. | 424/1.1 |
| 4,510,125 | 4/1985 | Grogg et al. | 424/1.1 |
| 4,564,472 | 1/1986 | Ueda et al. | 424/1.1 X |
| 4,705,849 | 11/1987 | Nunn et al. | 424/1.1 X |
| 4,755,375 | 7/1988 | Srivastava et al. | 424/1.1 |
| 4,857,299 | 8/1989 | Chia et al. | 424/1.1 |
| 5,032,678 | 7/1991 | Washino et al. | 424/1.1 X |
| 5,071,636 | 12/1991 | Yamauchi et al. | 424/1.1 |

OTHER PUBLICATIONS

Kelbaek, H., "Technetium-99m Labeling of Red Blood Cells: In Vitro Evaluation of a New Approach" *Journal of Nuclear Medicine*, vol. 27, No. 11, Nov. 1986, pp. 1770 to 1773.

*Primary Examiner*—Robert L. Stoll
*Assistant Examiner*—John M. Covert
*Attorney, Agent, or Firm*—Ladas & Parry

[57] ABSTRACT

A method of stabilizing a radiopharmaceutical complex composition is provided comprising the use of an element of Group VII of the Periodic Table selected from technetium, rhenium and manganese, or lanthanum or a transitional metal element or Rare Earth element with Atomic Number of 57 to 71 inclusive that has a range of valency states and an organic complexing compound which is capable of complexing with the radiopharmaceutical element defined above to provide a complex suitable for use in diagnosis and medical treatment, comprising the addition of sufficient of a pharmacologically acceptable weak oxidizing agent to stabilize the radiopharmaceutical complex composition. It is preferred to employ Technetium - 99m as the radiopharmaceutical element, the hemaxmethyl derivative of propyleneamineoxime as the complexing compound and sodium hypochlorite as the weak oxidizing agent. A stabilized composition comprising the same components is also provided.

22 Claims, No Drawings

STABILIZATION OF RADIOPHARMACEUTICAL COMPOSITIONS

This is a continuation of copending application Ser. No. 07/521,138 filed on May 8, 1990, now abandoned.

This invention relates to the stabilisation of radiopharmaceutical complex compositions and more particularly to the stabilisation of technetium - 99m labelled lipophilic complexes such as Exametazime (d.l. isomer of hexamethylpropyleneamine oxime).

According to the present invention there is provided a method of stabilising a radiopharmaceutical complex composition containing a radiopharmaceutical element of Group VII of the Periodic Table selected from technetium, rhenium and manganese, or lanthanum or a transitional metal element or a Rare Earth element with an Atomic Number of 57 to 71 inclusive that has a range of valency states and an organic complexing compound selected from the group consisting of propyleneamineoximes, mercaptoacetyl triglycines, bisaminothiols, kethoxal bisthiosemicarbazones and ethyl cysteinate dimers which is capable of complexing with the radiopharmaceutical element to form a complex suitable for use in diagnosis and medical treatment, or is a boronic acid adduct of technetium oxime comprising the addition of the radiopharmaceutical complex composition of a sufficient amount of a pharmaceutically acceptable weak oxidising agent to stabilise the radiopharmaceutical complex composition.

According to a further aspect of the present invention there is provided a stabilised radiopharmaceutical complex composition comprising a boronic acid adduct of technetium oxime or a radiopharmaceutical element of Group VII of the Periodic Table selected from technetium, rhenium and manganese, or lanthanum or a transitional metal element or a Rare Earth element with an Atomic Number of 57 to 71 inclusive that has a range of valency states, an organic complexing compound selected from the group consisting of propyleneamineoximes, mercaptoacetyl triglycines, bisaminothiols, kethoxal bisthiosemicarbazones and ethyl cysteinate dimers which is capable of complexing with the radiopharmaceutical element or a boronic acid adduct of technetium oxide to form a complex suitable for use in diagnosis and medical treatment and a sufficient amount of a pharmacologically acceptable weak oxidising agent to stabilise the radiopharmaceutical complex composition.

The radiopharmaceutical elements which can be used in the invention comprise (a) the elements of Group VII of the Periodic Table i.e. technetium, rhenium and manganese, and (b) Lanthanum and the transitional metal elements or Rare Earth elements with Atomic Numbers of 57 to 71 inclusive that have a range of valency states especially Gadolinium.

The ligand which may be employed to form a complex with the radiopharmaceutical element is an organic complexing compound which is capable of complexing with the radiopharmaceutical element defined above to provide a complex suitable for use in diagnosis and medical treatment. It serves to carry the radiopharmaceutical to the target organ within the human or animal body.

The weak oxidising agent to be employed in the invention comprises a sufficient amount of a pharmacologically acceptable oxidising agent to stabilise the radiopharmaceutical complex composition. Sodium hypochlorite is the preferred oxidising agent but other chlorine releasing substances such as chloramine, chlorinated lime, halzone, oxychlorosene and sodium dichlorisocyanurate may also be used in diluted solutions. All these are known for their low toxicity. Further halogen releasing agents which can be employed are iodine, iodophores and povidone-iodine. In addition acetic acid, boric acid and borax as well as dilute solutions of the strong oxidising agents such as peracetic acid and the peroxides and permanganates may also be used in the invention.

The radiopharmaceutical complex composition employed in the invention will normally contain an excess of the stannous, ferrous or cuprous ions used in the reduction of the radiopharmaceutical element to the appropriate valency state for complexing to occur but this reducing process could also be carried out by an electrochemical reducing technique.

According to a preferred aspect of the invention there is provided a method of stabilising a Technetium 199m neutral lipophilic complex containing stannous ions by the addition of a weak oxidising agent.

It is particularly preferred that the neutral lipophilic complex should be a derivative of propyleneamineoxime (especially the hexamethyl derivative), a mercaptoacetyl-triglycine, a bisaminothiol or a kethoxal bisthiosemicarbazone.

From the many radionuclides that are available it has been found that few have the radionucline properties that are required for use as pharmaceuticals in the measurement of physiological functions of an organ of the body.

Technetium -99m in one or another chemical form is employed in more than 90% of all nuclear medicine scans because of its ability to form stable complexes with a wide variety of ligands containing diverse donor atoms (O, N, S, P, As, Cl, etc.). From the chemical point of view Technetium behaves very like the element rhenium and to a lesser extent like manganese. Even in aqueous solution slight chemical differences affect the relative stabilities of the various oxidation states of technetium which exhibit a variety of geometrical structures. The technetium -99m complexes are preferred because of their physical properties including a half-life of 6 hours, a pure gamma energy of 140 KeV external photon and a yield of 90%. The technetium 99m complexes are readily obtained as sodium pertechnetate from molybdenum (Mo-99) generator absorbed on an alumina column. The column is composed of aluminum oxide which holds the molybdic oxide efficiently.

Technetium 99m is formed from the decay of Molybdenum 99 and a saline solution can be employed to release or elute the technetium from the column as the pertechnetate (TcO$_4$). The column can be eluted daily or on demand for about one week.

The pertechnetate is the only known Tc-(VII) compound stable in aqueous solution. However, in the presence of appropriate ligands pertechnetate may be reduced to give stable complexes in lower oxidation states (III or V in most cases). Many of these complexes have proved to be useful radiopharmaceuticals. The most commonly used reducing agent is the stannous ion added in the form of stannous chloride, fluoride or tartrate.

For convenience diagnostic radiopharmaceutical kits were designed to replace the early radiopharmaceutical compositions which were prepared from the constituent chemicals. Diagnostic kits typically consist of a vial containing pre-dispensed, sterile, non-pyrogenic, freeze-dried ingredients to which sodium pertechnetate solution is added. The main ingredients are normally chelate moieties (ligand), metallic ions (predominantly stannous ions), pH buffers and occasionally antioxidants such as ascorbic acid or gentisic acid. The actual quantities of material involved are very small. A typical preparation contains approximately $10^{-9}$M technetium and the reagents are often in excess by up to $10^6$ times. The kinetics and chemistry of reduction and complex formation influence the radiochemical purity. In order to obtain optimal performance each system has to be individually examined and stannous ions titrated such that pertechnetate is reduced to the required oxidation state for complex formation without side reactions of either tin or technetium taking place. This problem is further exacerbated by the presence of oxidants added during the processing of Mo-99 for Tc-99m generator sources and also the presence of oxygen. This has been indicated as a major cause of in vitro instability of diagnostic kits. The use of higher activity Mo-99 Tc-99m generators, the introduction of fusion-produced molybdenum generators of high specific activity and the increasing popularity of instant pertechnetate from high specific activity sources all involve radiation doses capable of reducing the pertechnetate. They require increased oxidants to maintain high Tc-99m extraction or elution yield. Therefore diagnostic kits of stannous (II) ion content become extremely difficult to design for universal use as the oxidants particularly in generators can vary considerably between manufacturer. The most susceptible kits are the so called "Low stannous kits". These are designed with a view to using with a relatively small amount of Tc-99m activity—this includes many new kits (Tc-99m mercaptoacetyltriglycine and Tc-99m Exametazime). In vitro instability of low-Sn (II)chelates can be minimised by nitrogen purging of the saline eluant and the diagnostic kit vials, in order to reduce the oxygen content before adding the pertechnetate. Another method is simply to increase the level of Sn(II) ion to counteract the oxidants, but many papers have reported altered activity distributions clinical scans for up to 2 weeks after administration of agents containing high levels of tin, which is most undesirable if the patient's progress is being followed with repeated scanning or if the patient is to receive other radiopharmaceuticals. The use of antioxidants such as ascorbic acid does help in eliminating the interfering oxidants without abandoning the low levels of Sn(II) ion needed to maintain the high selectivity of these radiopharmaceuticals.

Recently, much work has been carried out on molecules capable of transporting Tc-99m across the intact blood-brain barrier (BBB), with a view to routine use as a regional cerebral blood flow markers. However, very few molecules have been found which show this property. Most work has centered on the derivatives of propylene amine oxime (PnAO), bisaminothiol, (BAT) and kethoxal bisthiosemicarbazone (KTS). These form neutral and lipophilic complexes with Tc-99m which have been shown to penetrate the BBB by passive diffusion. The main problem with all these neutral lipophilic Tc-99m complexes is chemical instability due to conversion to less lipophilic species occuring even in aqueous media containing only the complex, excess ligand and a small amount of stannous ions. The conversion rate can be greatly accelerated by the addition of reducing agents.

Preliminary extraction efficiency using the methylated PnAO series suggested that the Tc-99m complex of Hexamethyl-PnAO (HMPOA) would be the superior molecule. Later it was shown that the HMPAO had chiral centres at C-2 and C-8 of the ligand and gave rise to meso and d,l diastereo-isomers and that the d,l form is superior in terms of brain retention and minimal redistribution. It is consequently now preferred and is available as a commercial kit called Ceretec (Tc-99m Exametazime). This agent is particularly useful for assessing regional cerebral blood flow in patients with neurological disorders as well as for labelling blood components such as leucocytes with a view to detecting sites of inflammation and abcess. The major limitations of these relatively expensive and useful radiopharmaceuticals is the extremely short in-vitro shelf life of the prepared kits—that is of the order of 30 minutes.

EXPERIMENTAL

Currently the only diagnostic kit formulation available as an example of a neutral lipophilic complex is the propyleneaminoxime derivative the d,l Hexamethyl-propyleneamineoxime (HMPAO). This will be referred to as Tc-99m Exametazime or Ceretec which is its trade name. Ceretec is a lyophilised formulation containing 0.5 mg d,l-HMPAO, 7.6 mg stannous chloride dihydrate and 4.5 mg sodium chloride sealed in a glass vial under nitrogen atmosphere. Each vial can be reconstituted with 5 ml of fresh Tc-99m eluate (from an eluate that is less than 2 hours old, previously from a generator which has been eluted within 24 hours) containing up to 1.11 GBq (30 mCi) of Tc-99m. Whilst preparing these kits care is taken not to introduce oxygen into the vial.

Throughout the experimental work the analysis of the neutral-lipophilic complex Tc-99m Exametazime and its three main impurities, hydrophilic complex, free pertechnetate and reduced -hydrolysed technetium -99m (R—H) were measured using a three phase chromatography system. This system consisted of two Gelman ITLC/SG strips, one run in butanone, where the lipophilic HMPAO and free pertechnetate migrated with the solvent, and the second strip was run in normal saline (sodium chloride 0.9% $^w/_v$), where the free pertechnetate migrated with the solvent. The third system used Whatman No. 1 paper and ran in freshly prepared 50% acetonitrile solution where the complex and impurities moved with the solvent front except for the reduced-hydrolysed-technetium.

To aid preliminary measurements and experiments a Whatman No. 1 strip was run in diethylether and this system quantified the amount of lipophilic complex only. The neutral lipophilic complex moved with the solvent front leaving at the base all the impurities including the hydrophilic complex.

Quantity control tests for radiochemical purity on these kits showed a mean percent of lipophilic complex of Tc-99m d,l HMPAO of 86% ±5% immediately following reconstitution. It was observed that during the decomposition period the free pertechnetate and the secondary complex were the main impurities in the first hour, after which only free pertechnetate continued to increase. A radiopharmaceutical purity limit of 80% was reached within 30 minutes of Kit preparation being reconstituted with fresh Tc-99m Eluate. These results were comparable with those published by Hung J C et al, 1988 J. Nucl. Med. 29;1568. All results presented are the means of three studies. Table one shows results of a typical breakdown of Tc-99m HMPAO.

TABLE I

| Time: (Min) | 0 | 15 | 30 | 45 | 60 | 90 | 120 | 180 |
|---|---|---|---|---|---|---|---|---|
| % Lipophilic Tc-99 m HMPAO: | 89.29 | 83.94 | 75.89 | 66.36 | 61.35 | 46.03 | 40.18 | 35.27 |

It has been shown that the instability of the complex could be promoted by excess stannous ion and it has been suggested that the stability of complexes may be improved by minimising the excess stannous ion. In addition, buffering the solution at a pH lower than 9 also improved stability.

Before considering any modifications of these diagnostic Kits, it was thought that the simplest way to reduce the rate of decomposition might be to decrease the storage temperature. The above figures are based on storage of radiopharmaceutical Kits after reconstitution in a refrigerator at a temperature of 10°–15° C. Therefore an experiment was set up to assess the effect of temperature on these Kits by storing the Kits after reconstitution with Tc-99m in the freezer section of the refrigerator which had a temperature of 2°–4° C. Samples were taken at the times indicated and the Kit replaced in the freezer section immediately after the sample collection. The sample was then analysed for radiochemical purity as described above using the three phase chromatography system. The following results were obtained:

TABLE II

| Time (Min): | 0 | 15 | 30 | 60 | 90 | 120 | 180 |
|---|---|---|---|---|---|---|---|
| % Lipophilic Tc-99 m HMPAO: | 88.80 | 85.80 | 81.10 | 71.46 | 68.38 | 71.58 | 66.02 |

The results indicate a rate of decomposition of 0.083 (±0.025)% per minute. This is a typical result based on the Arrhenius' equation which states that there is an exponential relationship between temperature and the rate of reaction.

Chemical intervention was next considered. The Ceretec Kit was reconstituted as usual and after 2 minutes of reconstitution 0.1 mg per 1 ml of freshly prepared ascorbic acid (B.P) was added; The vial was shaken for 10 seconds and then stored in the refrigerator at 10°–15° C. Samples were collected at the times indicated and analysed using the three phase chromatography system. Care was taken after sampling to return the vial to the lower temperature storage immediately. In addition it was ensured that air was not added to the vial whilst collecting the samples for analysis.

TABLE III

| | From time of reconstitution | | | | | | |
|---|---|---|---|---|---|---|---|
| Time (Mins): | 15 | 30 | 45 | 60 | 90 | 120 | 180 |
| % Lipophilic Tc-99 m HMPAO: | 80.84 | 69.45 | 64.02 | 53.93 | 42.59 | 32.91 | 23.17 |

The use of ascorbic acid showed little change in the rate of degradation and in fact it even appears to prevent the formation of the Tc-99m HMPAO complex.

Instead of an antioxidant an oxidizing agent in a very dilute solution was next employed. The aim was to add the oxidizing agent between 3–5 minutes after the addition of sodium pertechnetate to the kit. Therefore removing the excess stannous (II) after the complexisation process involving Tc-99m pertechnetate and d,l,HMPAO ligand by the addition of a commonly available oxidizing agent in use in medicine such as sodium hypochlorite solution (commercially available as Milton's solution). Sodium hypochlorite was chosen not only for its wide availability but because it has been shown by workers like Henning Kelbaek 1986; J. Nucl. Med. 27:1770 that 0.1% $^w/_v$ sodium hypochlorite solution (less than 2 mls) used for Haematological purpose (with the final preparation as an injectable) was still safe for the human use. A 1 in 40 sodium hypochlorite solution (0.025% $^w/_v$) was used for preparing further dilutions.

A series of solutions were prepared using 1 in 40 dilution of sodium hypochlorite solution to give ×20, ×50, ×100, ×200 (i.e. $1.25 \times 10^{-3}$, $5 \times 10^{-4}$, $2.5 \times 10^{-7}$, and $1.25 \times 10^{-7}$ $^w/_v$ of sodium hypochlorite). These were then added at 3 minutes to freshly operated Tc-99m HMPAO in equal volumes and stored at room temperatures (20° C.). A sample of the original Tc-99m HMPAO was also kept as a control. Samples were collected at the times indicated and again care was taken not to introduce air into vials during sampling. The storage vials were sterile nitrogen-filled vials (Amersham). The following results were obtained:

TABLE IV

| Time after Reconstitution | Control | A $1.25 \times 10^{-3w}/v$ | B $5 \times 10^{-3w}/v$ | C $2.5 \times 10^{-7w}/v$ | D $1.25 \times 10^{-7w}/v$ |
|---|---|---|---|---|---|
| 5 Mins. | 85.60 | 84.71 | 83.52 | 83.73 | 83.91 |
| 30 | 74.86 | 74.51 | 77.90 | 75.27 | 76.60 |
| 60 | 54.64 | 69.39 | 69.28 | 72.79 | 78.48 |
| 90 | 46.79 | 57.60 | 69.49 | 66.91 | 73.86 |
| 120 | 40.01 | 52.43 | 61.27 | 55.21 | 65.13 |
| 180 | 35.38 | 44.29 | 55.29 | 51.24 | 61.13 |

From these results it appears that the more dilute solutions of sodium hypochlorite were having the desired effect. It seems that the $1.25 \times 10^{-7}$ $^w/_v$ solution of sodium hypochlorite when stored in equal volume with the reconstituted Tc-99m HMPAO was the best choice. From the toxicity point of view the lower the concentration of sodium hypochlorite the less likely it is to produce any adverse reactions. During the experiments pH changes were noted using Neutralit strips from E.MERCK (F.R. Germany). There was no observable change in the pH which was approximately 6.5 whilst using sodium pertechnetate from a Mallinckrodt, Ultratechnekow TM generator for addition to the Ceretec vial. It is expected that the amount of sodium hypochlorite required for addition would vary slightly between generators because of the differences in oxidizing effect that the eluate from different generators would have.

Further studies were undertaken to investigate the effect of combining the effect of freezing with the addition of sodium hypochlorite and storing the penetration in the freezer section (2°-4° C.) the following results were obtained:

TABLE V

| Time (Mins) after Reconstitution: | 15 | 30 | 60 | 90 | 120 | 180 |
|---|---|---|---|---|---|---|
| % Lipophilic Tc-99 m HMPAO: | 93.00 | 85.56 | 85.19 | 82.14 | 87.22 | 82.74 |

The combination of freezing with the addition of sodium hypochlorite had the effect of reducing the rate of degradation of Tc-99m HMPAO to 0.036% per minute. Chromatographic analysis showed that there was a marked difference (of at least three fold) in the reduction of the rate of build-up of secondary hydrophilic complex and free pertechnetate compared with controls under the same conditions but without the addition of sodium hypochlorite.

To facilitate the preparation of fresh solutions of sodium hypochlorite, with a view to routine usage, the dilution factors were adjusted. It was considered much easier to prepare a $3.125 \times 10^{-3} w/v$ solution of sodium hypochlorite of which 0.1 ml would be added to a reconstituted Kit of Tc-99m HMPAO after 3 minute of reconstitution with fresh Tc-99m pertechnetate. In other words using a diabetic syringe where 1 ml is equal to 100 units; 12.5 units of 0.025% $w/v$ solution of sodium hypochlorite would be made up with water for injection to a volume of 100 units. After mixing 10 units (0.1 ml) would be added to a Kit of Tc-99m HMPAO.

Earlier it was mentioned that the vial of Ceretec would have to be prepared with fresh Tc-99m pertechnelate eluate (i.e. not more than 2 hours old) from a generator which has previously been eluted within 24 hours. The main reason for this was that the use of fresh generator eluate avoids the detrimental effects of oxidizing species which are present in the eluate or appear during eluate ageing due to radiolysis. It has been recently shown by Bayne V J et al, 1989; Nucl. Med. Commun. 10:29 that the addition of 0.4 mg of sodium iodide to fresh eluate per vial of the Ceretec can overcome the eluate age restriction. This was a particularly important development for certain nuclear medicine departments as they were supplied by central radiopharmacies. Even with the best transportation means many departments could not meet the eluate age limit. Either sodium iodide or potassium iodide can be used but potassium iodide has the advantage of being endothermic and therefore causes a drop in temperature as compared to sodium iodide, which causes an increase in temperature. The main disadvantage of the potassium salt is that if there is a calculation error then since the final preparation is to be injected it would have very serious consequences.

An experiment was carried out in which sodium iodide was added to fresh eluate from a generator eluated in the previous 24 hours. This eluate was kept for six hours and from it 1.1 GBq of Tc-99m pertechnetate was used to prepare Tc-99m HMPAO vial. The vial was reconstituted in the normal way except that 0.4 mg of sodium iodide was also present. After 3 minutes 0.1 ml of $3.125 \times 10^{-3} w/v$ solution of sodium hydrochloride was added to the vial. The vial was shaken for 10 seconds and then placed in the freezer section of the refrigerator (2°-4° C.). Samples were taken from the vial at the times indicated. These samples together with the samples of the control (i.e. without sodium hydrochloride) were analysed using a three phase chromatography system as described. Care was taken not to introduce air to the vials at any step. The following results were obtained:

TABLE VI

| Time after Reconstitution | % Lipophilic Tc-99 Am HMPAO Control | Addition of Sodium Hypochlorite |
|---|---|---|
| 3 Minutes | 91.20 | 89.16 |
| 30 | 85.96 | 86.27 |
| 60 | 76.69 | 89.04 |
| 90 | 60.78 | 87.13 |
| 120 | 57.10 | 88.91 |
| 150 | 50.64 | 85.28 |
| 180 | 51.35 | 86.78 |
| 240 | 49.59 | 83.62 |
| (21.5 hrs) 1290 | 21.32 | 58.64 |

The conclusion that can be drawn from all these was that incorporating each step of development (freezing, addition of sodium hypochloride, and the addition of sodium iodide to the eluate) neutral-lipophilic kit of Tc-99m HMPAO could be stablised for use up to eight hours after reconstitution with Tc-99m pertechnetate using the above procedure.

Although the present invention has been described in some detail by way of illustration and example for purpose of clarity and of undertanding, it will be obvious that certain changes and modifications may be practised.

This invention can be applied to existing diagnostic kits, as well as for many developing radiopharmaceuticals where optimal performance of the radiopharmaceutical can only be achieved by the control of stannous (II) titration. An example of an existing Kit which can benefit is the Tc-99m mercaptoacetyl triglycine Kit (MAG3) where because of its usage as a renal radiopharmaceutical high specific activity may be necessary to obtain optimal clinical results and where high stannous (II) may be a problem as its prime clinical application is to follow transplanted kidney function. Amongst the newer applications for the use of this invention are included the derivatives of propylenamine oxime, derivatives of bisaminothiol (BAT), derivatives of Kethoxal bisthiosemicarbazone (KTS), Boronic acid adducts of technetium oximes (BATOS), derived of ethyl cysteinate dimers (ECD).

This invention may be applicable for diagnostic Kits containing other metals such as copper (II) or Iron (II), instead of stannous (II).

In the chemistry of Rhenium, which has similar properties to technetium it should be possible to apply this invention to future Rhenium radiopharmaceuticals.

I claim:

1. A method of stabilizing a radiopharmaceutical complex composition containing a boronic acid adduct of technetium oxime or a radiopharmaceutical element of Group VII of the Periodic Table selected from technetium, rhenium and manganese, or lanthanum or a transitional metal element or a Rare Earth element with an Atomic Number of 57 to 71 inclusive that has a range of valency states complexed with an organic complexing compound selected from the group consisting of propyleneamineoximes, mercaptoacetyl triglycines, bisaminothiols, kethoxal bisthiosemicarbazones and ethyl cysteinate dimers, comprising the addition to the radiopharmaceutical complex composition of a sufficient amount of a pharmacologically acceptable weak oxidizing agent selected from the group consisting of sodium hypochlorite, chloramine, chlorinated lime, halazone, oxychlorosene, sodium dichloroisocyanurate, iodine, iodophores, povidone-iodine, acetic acid, boric acid and borax to stabilize the radiopharmaceutical complex composition.

2. A method of stabilising a radiopharmaceutical complex composition as claimed in claim 1 in which the radiopharmaceutical element is selected from technetium, rhenium and manganese.

3. A method of stabilising a radiopharmaceutical complex composition as claimed in claim 2 in which the radiopharmaceutical element is Technetium-99m.

4. A method of stabilising a radiopharmaceutical composition as claimed in claim 1 in which the organic complexing compound is selected from a propyleneamineoxime, a mercaptoacetyltriglycine, a bisaminothiol or a kethoxal bisthiosemicarbazone.

5. A method of stabilising a radiopharmaceutical composition as claimed in claim 4 in which the radiopharmaceutical element is Technetium-99m.

6. A method of stabilising a radiopharmaceutical complex composition as claimed in claim 5 in which the organic complexing compound is the hexamethyl derivative of propyleneamineoxime.

7. A method of stabilising a radiopharmaceutical complex composition as claimed in claim 1 in which the pharmacologically acceptable weak oxidising agent is a chlorine-releasing substance.

8. A method of stabilising a radiopharmaceutical complex composition as claimed in claim 7 in which the weak oxidising agent is sodium hypochloride.

9. A method of stabilising a radiopharmaceutical complex composition as claimed in claim 8 in which the radiopharmaceutical element is Technetium -99m.

10. A method of stabilizing a radiopharmaceutical complex composition comprising stannous ions and a complex of technetium-99m with the hexamethyl derivative of propyelenamineoxime said method comprising addition of a sufficient amount of sodium hypochlorite to stabilize the radiopharmaceutical complex composition.

11. A stabilized radiopharmaceutical complex composition comprising a boronic acid adduct of technetium oxime or a radiopharmaceutical element of Group VII of the Periodic Table selected from technetium, rhenium and manganese, or lanthanum or a transitional metal element or a Rare Earth element with an Atomic Number of 57 to 71 inclusive that has a range of valency states, complexed with an organic complexing compound selected from the group consisting of propyleneamineoximes, mercaptoacetyl triglycines, bisaminothiols, kethoxal bisthiosemicarbazones and ethyl cysteinate dimers and a sufficient amount of a pharmacologically acceptable weak oxidizing agent selected from the group consisting of sodium hypochlorite, chloramine, chlorinated lime, halazone, oxychlorsene, sodium dichloroisocyanide, iodine, iodophores, povidone-iodine, acetic acid, boric acid and borax to stabilize the radiopharmaceutical complex composition.

12. A stabilised radiopharmaceutical complex composition as claimed in claim 11 in which the radiopharmaceutical element is selected from technetium, rhenium and manganese.

13. A stabilised radiopharmaceutical complex composition as claimed in claim 12 in which the radiopharmaceutical element is Technetium -99m.

14. A stabilised radiopharmaceutical composition as claimed in claim 11 in which the organic complexing compound is selected from a propyleneamineoxime, a mercaptoacetyltriglycine, a bisaminothiol or a kethoxal bisthiosemicarbazone.

15. A stabilised radiopharmaceutical composition as claimed in claim 11 in which the radiopharmaceutical element is Technetium - 99m.

16. A stabilised radiopharmaceutical complex composition as claimed in claim 15 in which the organic complexing compound is the hexamethyl derivative of propyleneamineoxime.

17. A stabilised radiopharmaceutical complex composition as claimed in claim 11 in which the pharmacologically acceptable weak oxidising agent is a chlorine-releasing substance.

18. A stabilised radiopharmaceutical complex composition as claimed in claim 17 in which the weak oxidising agent is sodium hypochlorite.

19. A stabilised radiopharmaceutical complex composition as claimed in claim 18 in which the radiopharmaceutical element in Technetium -99m.

20. A stabilized radiopharmaceutical complex composition comprising a complex of technetium-99m with the hexamethyl derivative of propyleneamineoxime, stannous ions and a sufficient amount of sodium hypochloride to stabilize the radiopharmaceutical complex composition.

21. A method of stabilizing a radiopharmaceutical complex composition containing a boronic acid adduct of technetium oxime or a radiopharmaceutical element of Group VII of the Periodic Table selected from technetium, rhenium and manganese, or lanthanum or a transitional metal element or a Rare Earth element with an Atomic Number of 57 to 71 inclusive that has a range of valency states complexed with an organic complexing compound selected from the group consisting of propyleneamineoximes, mercaptoacetyl triglycines, bisaminothiols, kethoxal bisthiosemicarbazones and ethyl cysteinate dimers, comprising the addition to the radiopharmaceutical complex composition of a sufficient amount of dilute solution of an oxidising agent selected from the group consisting of peracetic acid, and pharmaceutically acceptable peroxides, and permanganates to stabilize the radiopharmaceutical complex composition.

22. A stabilized radiopharmaceutical complex composition comprising a boronic acid adduct of technetium oxime or a radiopharmaceutical element of Group VII of the Periodic Table selected from technetium, rhenium and manganese, or lanthanum or a transitional metal element or a Rare Earth element with an Atomic Number of 57 to 71 inclusive that has a range of valency states, complexed with an organic complexing compound selected from the group consisting of propyleneamineoximes, mercaptoacetyl triglycines, bisaminothiols, kethoxal bisthiosemicarbazones and ethyl cysteinate dimers and a sufficient amount of a dilute solution of an oxidizing agent selected from the group consisting of peracetic acid, pharmacologically acceptable peroxides and permanganates to stabilize the radiopharmaceutical complex composition.

* * * * *

UNITED STATES PATENT AND TRADEMARK OFFICE
CERTIFICATE OF CORRECTION

PATENT NO. : 5,262,175
DATED : November 16, 1993
INVENTOR(S) : Kishor K. SOLANKI It is certified that error appears in the above-indentified patent and that said Letters Patent is hereby corrected as shown below:

On the title page, left column, in the Abstract, line 15, "hemaxmethyl" should be -- hexamethyl --.

Col. 9, line 59, (claim 11) "dichloroisocyanide" should be -- dichloroisocyanurate --.

Signed and Sealed this

Twentieth Day of September, 1994

Attest:

BRUCE LEHMAN

Attesting Officer

Commissioner of Patents and Trademarks